US012678046B2

(12) United States Patent
Lee et al.

(10) Patent No.: US 12,678,046 B2
(45) Date of Patent: Jul. 14, 2026

(54) WEARABLE ELECTRONIC APPARATUS INCLUDING A BACK COVER STRUCTURE CONSIDERING OPTICAL SENSOR

(71) Applicant: Samsung Electronics Co., Ltd., Suwon-si (KR)

(72) Inventors: Jeahyuck Lee, Suwon-si (KR); Hyunguk Yoo, Suwon-si (KR); Injo Jeong, Suwon-si (KR); Seongwook Jo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 163 days.

(21) Appl. No.: 18/353,473

(22) Filed: Jul. 17, 2023

(65) Prior Publication Data

US 2023/0355098 A1 Nov. 9, 2023

Related U.S. Application Data

(63) Continuation of application No. PCT/KR2021/002123, filed on Feb. 19, 2021.

(30) Foreign Application Priority Data

Feb. 17, 2021 (KR) ........................ 10-2021-0021168

(51) Int. Cl.
*A61B 5/00* (2006.01)
*G04G 21/02* (2010.01)
(52) U.S. Cl.
CPC ............ *A61B 5/0059* (2013.01); *A61B 5/681* (2013.01); *G04G 21/025* (2013.01)
(58) Field of Classification Search
CPC ....... A61B 5/0059; A61B 5/681; A61B 5/332; A61B 5/02427; A61B 5/02438;
(Continued)

(56) References Cited

U.S. PATENT DOCUMENTS

2011/0004106 A1 1/2011 Iwamiya et al.
2014/0223359 A1 8/2014 Yamada
(Continued)

FOREIGN PATENT DOCUMENTS

EP 3871588 B1 * 6/2025 ............. A61B 5/743
JP 2011-147746 A 8/2011
(Continued)

OTHER PUBLICATIONS

Extended European Search Report dated Mar. 26, 2024, issued in European Patent Application No. 219268398.1113.
(Continued)

*Primary Examiner* — Ankit D Tejani
*Assistant Examiner* — Joshua Brendon Solomon
(74) *Attorney, Agent, or Firm* — Jefferson IP Law, LLP

(57) ABSTRACT

An electronic apparatus is provided. The electronic apparatus includes a sensor that includes a light emitting unit and a light receiving unit, a transparent layer that includes a first transparent layer including first plastic having light transmittance, disposed to cover the sensor, and transmitting light emitted from the light emitting unit for detecting a signal related to biometric information, and a second transparent layer transmitting light entering the light receiving unit, a cover that includes at least one partition wall including second plastic having lower light transmittance than the first plastic and separating the first transparent layer and the second transparent layer from each other, and a processor that acquires the biometric information based on the signal related to the biometric information received through the light receiving unit.

18 Claims, 12 Drawing Sheets

(58) Field of Classification Search

CPC ... A61B 5/256; A61B 5/28; A61B 2562/0238; A61B 2562/146; G04G 21/025; G04G 17/06

See application file for complete search history.

(56) References Cited

U.S. PATENT DOCUMENTS

| | | | |
|---|---|---|---|
| 2014/0275854 | A1 | 9/2014 | Venkatraman et al. |
| 2014/0278229 | A1 | 9/2014 | Hong et al. |
| 2015/0355604 | A1 | 12/2015 | Fraser et al. |
| 2016/0022203 | A1 | 1/2016 | Arnold et al. |
| 2016/0103985 | A1 | 4/2016 | Shim et al. |
| 2016/0331252 | A1* | 11/2016 | Matsuo ................ A61B 5/6803 |
| 2016/0378069 | A1 | 12/2016 | Rothkopf |
| 2017/0135636 | A1 | 5/2017 | Park et al. |
| 2017/0296088 | A1 | 10/2017 | Choi |
| 2017/0315511 | A1 | 11/2017 | Shim et al. |
| 2018/0000362 | A1* | 1/2018 | Matsuo .............. A61B 5/02427 |
| 2018/0220534 | A1 | 8/2018 | Heikkinen et al. |
| 2018/0220972 | A1* | 8/2018 | Jeong ................... A61B 5/7475 |
| 2018/0228414 | A1 | 8/2018 | Shao et al. |
| 2019/0069848 | A1 | 3/2019 | Clavelle et al. |
| 2019/0072912 | A1* | 3/2019 | Pandya ................. G04G 21/025 |
| 2019/0074729 | A1* | 3/2019 | Wittenberg ............. H02J 50/10 |
| 2019/0082985 | A1 | 3/2019 | Hong et al. |
| 2019/0090806 | A1 | 3/2019 | Clavelle et al. |
| 2019/0101870 | A1 | 4/2019 | Pandya et al. |
| 2020/0229761 | A1 | 7/2020 | Pandya et al. |
| 2021/0244301 | A1* | 8/2021 | Ko ......................... A61B 5/742 |
| 2021/0361233 | A1 | 11/2021 | Wilson et al. |
| 2022/0151554 | A1 | 5/2022 | Jang et al. |

FOREIGN PATENT DOCUMENTS

| | | | |
|---|---|---|---|
| JP | 2014-180288 | A | 9/2014 |
| JP | 2016-086873 | A | 5/2016 |
| JP | 2016-148657 | A | 8/2016 |
| JP | 2020-202976 | A | 12/2020 |
| KR | 10-2016-0003458 | A | 1/2016 |
| KR | 10-2016-0041553 | A | 4/2016 |
| KR | 10-2017-0123205 | A | 11/2017 |
| KR | 10-2019-0139440 | A | 12/2019 |
| KR | 10-2021-0015250 | A | 2/2021 |

OTHER PUBLICATIONS

International Search Report dated Nov. 9, 2021, issued in International Patent Application No. PCT/KR2021/002123.

European Office Action dated Sep. 29, 2025, issued in a European Patent Application No. 21 926 839.8.

Korean Office Action dated Jan. 22, 2026, issued in Korean Patent Application No. 10-2021-0021168.

Chinese Office Action dated May 20, 2026, issued in Chinese Application No. 202180093926.8.

* cited by examiner

WEARABLE ELECTRONIC APPARATUS INCLUDING A BACK COVER STRUCTURE CONSIDERING OPTICAL SENSOR

CROSS-REFERENCE TO RELATED APPLICATION(S)

This application is a continuation application, claiming priority under § 365(c), of an International application No. PCT/KR2021/002123, filed on Feb. 19, 2021, which is based on and claims the benefit of a Korean patent application number 10-2021-0021168, filed on Feb. 17, 2021, in the Korean Intellectual Property Office, the disclosure of which is incorporated by reference herein in its entirety.

BACKGROUND

1. Field

The disclosure relates to a wearable electronic apparatus with a rear cover structure considering an optical sensor.

2. Description of Related Art

With increasing interest in health, functions for measuring a user's biometric information have been added to electronic apparatuses. In particular, a wearable electronic apparatus to be worn on a user's body, such as a wrist, includes various sensors capable of acquiring a user's biometric information, and thus has been required to have a structure for acquiring the biometric information more accurately and improving a user's wearing comfort.

The sensors added to the electronic apparatus should not be broken by external impact and should be resistant to life scratches. To this end, a cover may be separately provided to protect the sensors. The cover may be notched to provide a space for sensor mounting or improve functionality. In the case of using glass as the material of the cover, it may be difficult to perform polishing processing due to the nature of the glass. Further, scratches formed during the processing may reduce light transmittance, thereby increasing manufacturing costs or decreasing manufacturing yields.

In the case of the wearable electronic apparatus, the cover may be manufactured to have an outer surface having a large curvature so as to enhance a user's wearing comport. Even in this case, the glass cover may be whitened due to uneven polishing, thereby increasing manufacturing costs or decreasing manufacturing yields and thus decreasing mass productivity.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic apparatus including a cover that is easily manufactured and raise the efficiency of light transmittance.

Additional aspects will be set forth in part in the description which follows and, in part, will be apparent from the description, or may be learned by practice of the presented embodiments.

In accordance with an aspect of the disclosure, an electronic apparatus is provided. The electronic apparatus includes a sensor that includes a light emitting unit and a light receiving unit, a transparent layer that includes a first transparent layer including first plastic having light transmittance, disposed to cover the sensor, and transmitting light emitted from the light emitting unit for detecting a signal related to biometric information, and a second transparent layer transmitting light entering the light receiving unit, a cover that includes at least one partition wall including second plastic having lower light transmittance than the first plastic and separating the first transparent layer and the second transparent layer from each other, and a processor that acquires the biometric information based on the signal related to the biometric information received through the light receiving unit.

According to various embodiments of the disclosure, there is provided a cover that can receive a signal related to biometric information more efficiently, be easy to process, and be durable.

According to various embodiments of the disclosure, an improved optical structure and electrode layer are included to more accurately and precisely measure a user's biometric information, thereby decreasing manufacturing costs of the electronic apparatus, increasing manufacturing yields, and increasing mass productivity.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

The same reference numerals are used to represent the same elements throughout the drawings.

DETAILED DESCRIPTION

Figure 1:
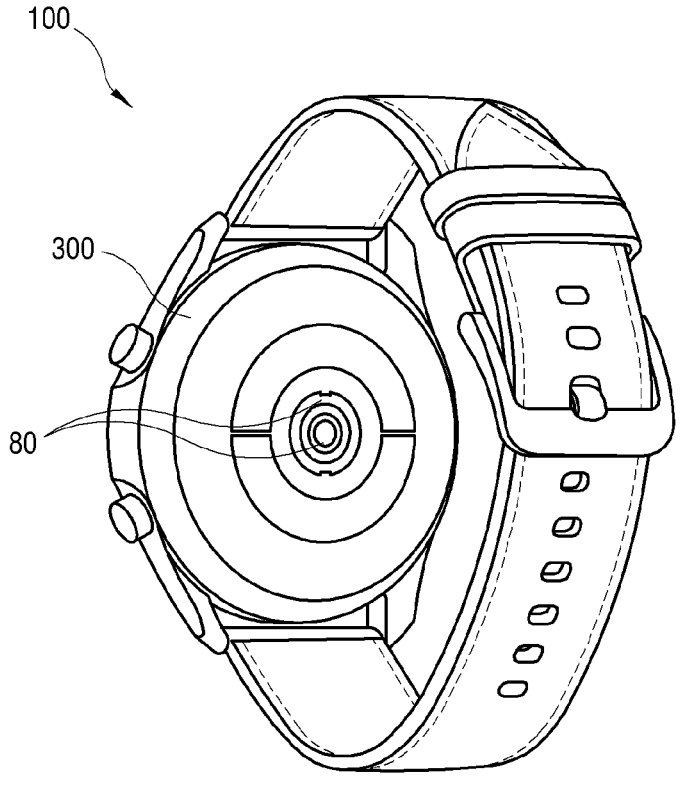
FIG. 1 illustrates an electronic apparatus according to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

According to various embodiments of the disclosure, there may be various types of an electronic apparatus. The electronic apparatus may, for example, include portable communication apparatuses (e.g., smartphones), computers, portable multimedia apparatuses, portable medical apparatuses, cameras, wearable apparatuses, or home appliances. The electronic apparatus according to an embodiment of the disclosure is not limited to the foregoing apparatuses.

Various embodiments of the disclosure and terms used therein are not intended to limit the technical features described in the disclosure, but required to be construed as including various modifications, equivalents or substitutions of the embodiments. In connection with the description of the drawings, like reference numerals may refer to similar or related elements. A singular form of a noun corresponding to an item may include one item or a plurality of items unless otherwise contextually indicated clearly. In this disclosure, "A or B", "at least one of A and B", "at least one of A or B", "A, B or C", "at least one of A, B and C", and "at least one of A, B, or C" and the like phrase may include any one of items listed together in the corresponding phrase, or all possible combinations thereof "first", "second", and the like terms may be used only for distinguishing an element from other elements, and these elements are not restricted in other aspects (e.g., importance or order). When it is mentioned that one (e.g., first) element is "coupled" or "connected" to another (e.g., second) element with or without terms of "functionally" or "communicatively", it means that one element may be connected to another element directly (e.g., by a wire), wirelessly, or through a third element.

The term "module" used in various embodiments of the disclosure may include a unit embodied in hardware, software or firmware, and is interchangeable with the terms such as, for example, logic, logic block, parts, or circuit. The module may be an integrally formed element, or a minimum unit of the element or a part of the minimum unit, which performs one or more functions. For example, according to an embodiment, the module may be embodied in the form of an application-specific integrated circuit (ASIC).

Various embodiments of the disclosure may be carried out by software (e.g., the program 30) including one or more instructions stored in a storage medium (e.g., an internal memory 221 or an external memory 222) readable by a machine (e.g., the electronic apparatus 100). For example, the processor (e.g., the processor 10) of the machine (e.g., the electronic apparatus 100) calls at least one instruction among one or more stored instructions from the storage medium, and execute the called instruction. This makes it possible for the machine to perform at least one function according to the at least one called instruction. The one or more instructions may include a code generated by a compiler or a code executable by an interpreter. The machine-readable storage medium may be provided in the form of a non-transitory storage medium. In the specification, 'non-transitory' merely means that the storage medium is tangible and does not include a signal (e.g., an electromagnetic wave), without distinguishing between a case where data is semi-permanently stored in the storage medium and a case where data is temporarily stored.

According to an embodiment, methods according to various embodiments of the disclosure may be provided as involved in a computer program product. The computer program product may be traded as a product between a seller and a buyer. The computer program product may be distributed in the form of a machine-readable storage medium (e.g., a compact disc read only memory (CD-ROM)) or may be directly or online distributed (e.g., downloaded or uploaded) between two user apparatuses (e.g., smartphones) through an application store (e.g., Play Store™). In the case of the online distribution, at least part of the computer program product may be transitorily stored or temporarily produced in a machine-readable storage medium such as a memory of a manufacturer server, an application-store server, or a relay server.

According to various embodiments, each element (e.g., the module or the program) of the foregoing elements may include a singular entity or a plurality of entities, and some among the plurality of entities may be separated and disposed in another element. According to various embodiments, one or more elements among the foregoing elements or operations may be omitted, or one or more other elements or operations may be added. Alternatively or additionally, a plurality of elements (e.g., the module or the program) may be integrated into a single element. In this case, the integrated element may perform one or more functions of the element among the plurality of elements equally or similarly to those performed by the corresponding element among the plurality of elements before the integration. According to various embodiments, operations performed by the module, the program or other elements may be executed in sequence, in parallel, repetitively, or heuristically, or one or more among the foregoing operations may be performed in different order, be omitted or additionally include one or more other operations.

FIG. 1 illustrates an electronic apparatus according to an embodiment of the disclosure.

The disclosure is applicable, but not limited, to various electronic apparatuses as described above. However, for convenience of description and ease of understanding, one of wearable electronic apparatuses, e.g., a smart watch will be described as the electronic apparatus 100 according to an embodiment of the disclosure.

Referring to FIG. 1, the electronic apparatus 100 according to an embodiment of the disclosure may be worn on a user's wrist, and a sensor module 80 may be disposed on the rear of the electronic apparatus 100 to acquire biometric information from the user's wrist being in contact with the electronic apparatus 100. The sensor module 80 according to another embodiment of the disclosure may be, but not limited to, an optical sensor, and/or an electrode sensor, and details thereof will be described later.

In the electronic apparatus 100, the sensor module 80 is required not to be broken by external impact and required to be resistant to life scratches. Further, the electronic apparatus 100 may be required to have a structure for acquiring the biometric information more accurately and improving a user's wearing comport.

To this end, the electronic apparatus 100 may include a cover 300 for protecting the sensor module 80. To acquire the biometric information more accurately, it may be necessary to minimize a distance between the outer surface of the cover 300 to be in contact with a user's body and the sensor module 80. Further, the smaller a contact area between the outer surface of the cover 300 and a user's body, the more comfortable a user's wearing.

Therefore, the outer surface of the cover 300 may have curvature in consideration of a user's wearing comfort and the efficiency of the sensor module 80. However, when the cover is made of glass, the larger the curvature of the outer surface the cover has, the more difficult it is to process and the easier it is to be broken by external impact.

Below, the electronic apparatus 100 will be described according to various embodiments of the disclosure, in which the cover 300 is made of plastic, thereby increasing an optical efficiency of a lens and being easily manufactured.

Figure 2:
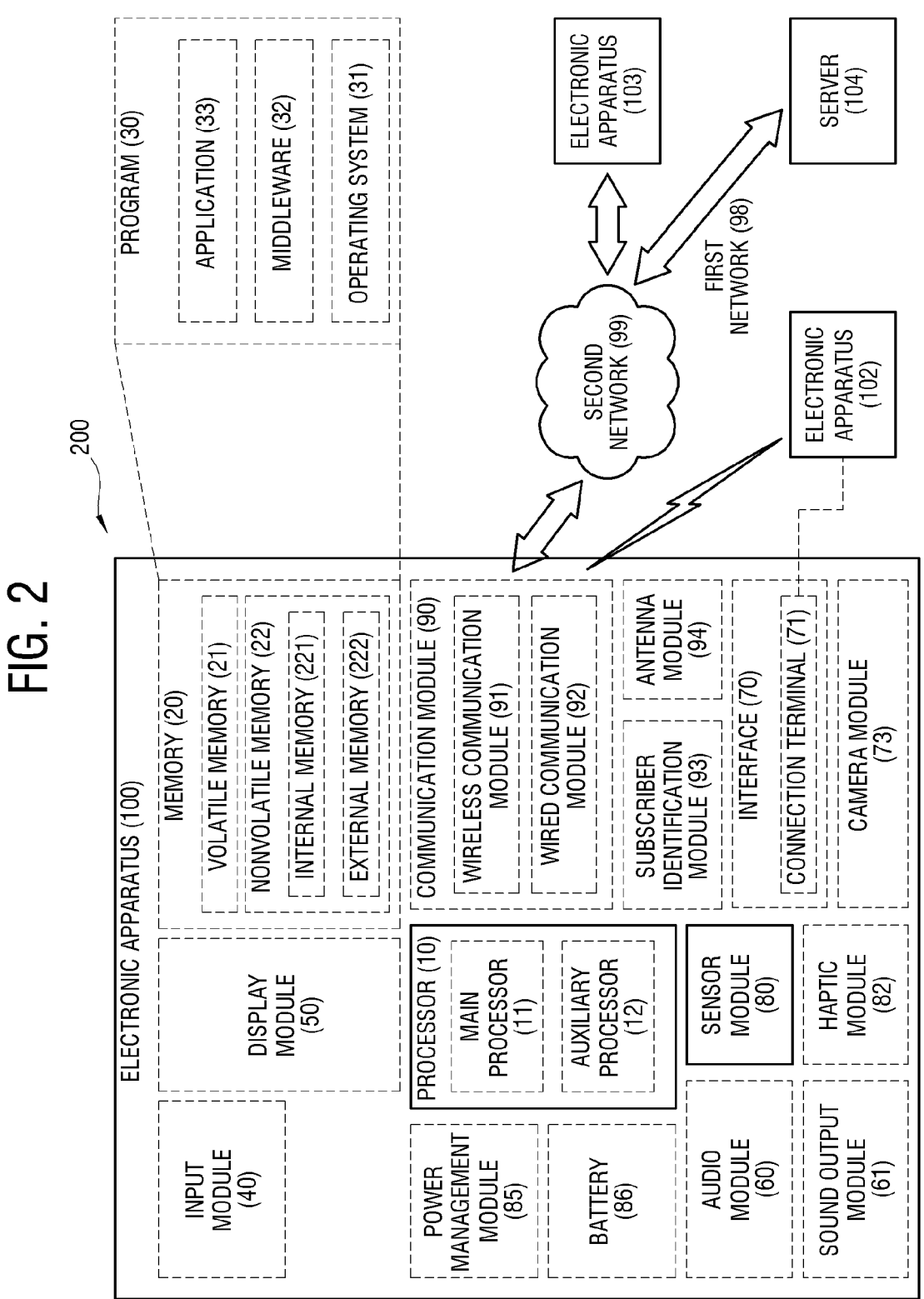
FIG. 2 is a block diagram of an electronic apparatus according to an embodiment of the disclosure.

FIG. 2 is a block diagram of an electronic apparatus according to an embodiment of the disclosure.

FIG. 2 is a block diagram of the electronic apparatus 100 in a network environment 200 according to various embodiments.

Referring to FIG. 2, under a network environment 200, the electronic apparatus 100 may communicate with an electronic apparatus 102 through a first network 98 (e.g., a short-range wireless communication network), or communicate with at least one of an external electronic apparatus 103 or a server 104 through a second network 99 (e.g., a long-range wireless communication network). According to an embodiment, the electronic apparatus 100 may communicate with the external electronic apparatus 103 through the server 104. According to another embodiment, the electronic apparatus 100 may include a processor 10, a memory 20, an input module 40, a display module 50, an audio module 60, a sound output module 61, an interface 70, a connection terminal 71, a camera module 73, a sensor module 80, a haptic module 82, a power management module 85, a battery 86, a communication module 90, a subscriber identification module 93, or the antenna module 94. According to an alternative embodiment, the electronic apparatus 100 may exclude at least one (e.g., the connection terminal 71) among these elements, or may additionally include one or more other elements. According to an alternative embodiment, some (e.g., the sensor module 80, the camera module 73, or the antenna module 94) among these elements may be integrated into one element (e.g., the display module 50).

The processor 10 may, for example, execute software (e.g., a program 30) to control at least one of other elements (e.g., a hardware or software element) of the electronic apparatus 100 connected to the processor 10, and perform various data processing or operations. According to yet another embodiment, as at least a part of the data processing or operations, the processor 10 may store a command or data received from other elements (e.g., the sensor module 80 or the communication module 90) in a volatile memory 21, processes the command or data stored in the volatile memory 21, and store result data in a nonvolatile memory 22. According to yet another embodiment, the processor 10 may include a main processor 11 (e.g., a central processing unit or an application processor), or an auxiliary processor 12 (e.g., a graphic processor, a neural processing unit (NPU), an image signal processor, a sensor hub processor, or a communication processor) operating independently of or in conjunction with the main processor 11. For example, when the electronic apparatus 100 includes the main processor 11 and the auxiliary processor 12, the auxiliary processor 12 may be configured to use less power than the main processor 11, or to be specialized for a designated function. The auxiliary processor 12 may be provided separately from the main processor 11 or as a part of the main processor 11.

The auxiliary processor 12 may, for example, control at least some of functions or states related to at least one element (e.g., the display module 50, the sensor module 80, or the communication module 90) among the elements of the electronic apparatus 100, instead of the main processor 11 while the main processor 11 is inactive (e.g., sleeping) or in conjunction with the main processor 11 while the main processor 11 is active (e.g., running an application). According to yet another embodiment, the auxiliary processor 12 (e.g., the image signal processor or the communication processor) may be provided as a part of other functionally related elements (e.g., the camera module 73 or the communication module 90). According to yet another embodiment, the auxiliary processor 12 (e.g., the neural processing unit) may include a hardware structure specialized for processing an artificial intelligence (AI) model. The AI model may be created through machine learning. Such learning may, for example, be performed in the electronic apparatus 100 itself, on which the AI model is applied, or be performed through a separate server (e.g., the server 104). The learning algorithm may, for example, include supervised learning, unsupervised learning, semi-supervised learning or reinforcement learning, but is not limited to these examples. The AI model may include a plurality of artificial neural network layers. The artificial neural network may include a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-networks, or one of combinations between two or more networks aforementioned, but is not limited to these examples. Besides the hardware structure, the AI model may additionally or alternatively include a software structure.

The memory 20 may be configured to store various pieces of data to be used by at least one element (e.g., the processor 10 or the sensor module 80) of the electronic apparatus 100. The data may, for example, include the software (e.g., the program 30), and input data or output data with regard to a command related to the software. The memory 20 may include the volatile memory 21 or the nonvolatile memory 22.

The program 30 may be stored as the software in the memory 20, and may for example include an operating system 31, a middleware 32, or an application 33.

The input module 40 may receive a command or data, which will be used by the element (e.g., the processor 10) of the electronic apparatus 100, from the outside (e.g., a user)

of the electronic apparatus 100. The input module 40 may, for example, include a microphone, a mouse, a keyboard, a key (e.g., a button), or a digital pen (e.g., a stylus pen).

The display module 50 may visually provide information to the outside (e.g., a user) of the electronic apparatus 100. The display module 50 may, for example, include a display, a hologram device or a projector, and a control circuit for controlling a corresponding one of the display, the hologram device or the projector. According to yet another embodiment, the display module 50 may include a touch the sensor configured to detect a touch, or a pressure the sensor configured to detect the strength of a force generated by the touch.

The audio module 60 may be configured to convert a sound into an electric signal, or reversely convert the electric signal into the sound. According to yet another embodiment, the audio module 60 may obtain a sound through the input module 40, or output a sound through the sound output module 61 or an external electronic apparatus (e.g., the electronic apparatus 102) (e.g., the loudspeaker or a headphone) directly or wirelessly connected to the electronic apparatus 100.

The sound output module 61 may output a sound signal to the outside of the electronic apparatus 100. The sound output module 61, for example, include a loudspeaker or a receiver. The loudspeaker may be used for general purposes such as multimedia playback or recording playback. The receiver may be used to receive an incoming call. According to yet another embodiment, the receiver may be provided separately from the loudspeaker or as a part of the loudspeaker.

The interface 70 may support one or more designated protocols that the electronic apparatus 100 may use to be directly or wirelessly connected to an external electronic apparatus (e.g., the electronic apparatus 102). According to yet another embodiment, the interface 70 may, for example, include a high-definition multimedia interface (HDMI), a universal serial bus (USB) interface, a secure digital (SD) card interface, or an audio interface.

The connection terminal 71 may include a connector through which the electronic apparatus 100 can physically connect with an external electronic apparatus (e.g., the electronic apparatus 102). According to yet another embodiment, the connection terminal 71 may, for example, include an HDMI connector, a USB connector, an SD card connector, or an audio connector (e.g., a headphone connector).

The camera module 73 may be configured to take a still image or a moving image. According to yet another embodiment, the camera module 73 may include one or more lenses, image the sensors, image signal processors, or flashes.

The sensor module 80 may be configured to detect operating states (e.g., power or temperature) of the electronic apparatus 100, or external environment states (e.g., a user's state), and generate electric signals or data values corresponding to the detected states. According to yet another embodiment, the sensor module 80 may, for example, include a gesture the sensor, a gyro the sensor, a barometer, a magnetic the sensor, an accelerometer, a grip the sensor, a proximity the sensor, a color the sensor, an infrared (IR) the sensor, a biometric the sensor, a temperature the sensor, a humidity the sensor, or an illuminance the sensor.

The haptic module 82 may be configured to convert an electric signal into a mechanical stimulus (e.g., vibration or movement) that a user can perceive through his/her tactile or kinetic senses. According to yet another embodiment, the haptic module 82 may, for example, include a motor, a piezoelectric device, or an electrical stimulation device.

The power management module 85 may manage power supplied to the electronic apparatus 100. According to yet another embodiment, the power management module 85 may, for example, be provided as at least a part of a power management integrated circuit (PMIC).

The battery 86 may supply power to at least one element of the electronic apparatus 100. According to yet another embodiment, the battery 86 may, for example, include a non-rechargeable primary cell, a rechargeable secondary cell, or a fuel cell.

The communication module 90 may be configured to establish a direct (e.g., wired) communication channel or a wireless communication channel between the electronic apparatus 100 and the external electronic apparatus (e.g., the electronic apparatus 102, the external electronic apparatus 103, or the server 104), and support communication through the established communication channel. The communication module 90 may include one or more communication processors that operate independently of the processor 10 (e.g., the application processor) and support the direct (e.g., wired) communication or the wireless communication. According to yet another embodiment, the communication module 90 may include a wireless communication module 91 (e.g., a cellular communication module, a short-range wireless communication module, or a global navigation satellite system (GNSS) communication module), or a wired communication module 92 (e.g., a local area network (LAN) communication module, or a power line communication module). Among these communication modules, a corresponding communication module may communicate with an external electronic apparatus 103 through the first network 98 (e.g., Bluetooth, Wi-Fi direct, infrared data association (IrDA) or the like short-range communication network) or the second network 99 (e.g., a legacy cellular network, a fifth generation (5G) network, the next-generation communication network, the Internet, a computer network (e.g., LAN or wide area network (WAN)) or the like long-range communication network). Such various types of communication modules may be integrated into one element (e.g., a single chip), or may be provided as a plurality of elements (e.g., a plurality of chips) separated from each other. The wireless communication module 91 may identify or authenticate the electronic apparatus 100 in the first network 98, the second network 99 or the like communication network, based on subscriber information (e.g., international mobile subscriber identity (IMSI)) stored in the subscriber identification module 93.

The wireless communication module 91 may support the 5G network after the fourth generation (4G) network and the next-generation communication technology, for example, new radio (NR) access technology. The NR access technology may support high-capacity and high-speed data transmission (enhanced mobile broadband (eMBB)), terminal power minimization and multiple terminal access (massive machine type communications (mMTC)), or ultra-reliable and low-latency communications (URLLC). The wireless communication module 91 may, for example, support a high frequency band (e.g., a millimeter wave (mmWave) band) to achieve a high rate of data transmission. The wireless communication module 91 may support various technologies for securing performance in the high frequency band, for example, beamforming, massive multiple-input and multiple-output (MIMO), full dimensional (FD)-MIMO, an array antenna, analog beam-forming, a large-scale antenna or the like technologies. The wireless communication module 91 may support various requirements stipulated in the electronic apparatus 100, the external electronic apparatus (e.g., the external electronic apparatus 103) or the network system (e.g., the second network 99). According to yet another embodiment, the wireless communication module 91 may support a peak data rate (e.g., 20 gigabits per second (Gbps) or higher) for realizing eMBB, a loss coverage (e.g., 164 dB or below) for realizing mMTC, or U-plane latency (e.g., a downlink (DL) and an uplink (UL) lower than 0.5 ms, or a round trip lower than 1 ms) for realizing URLLC.

The antenna module 94 may transmit or receive a signal or power to or from the outside (e.g., the external electronic apparatus). According to yet another embodiment, the antenna module 94 may include an antenna with a conductor formed on a substrate (e.g., a printed circuit board (PCB)) or a radiator formed of a conductive pattern. According to yet another embodiment, the antenna module 94 may include a plurality of antennas (e.g., an array antenna). In this case, at least one antenna suitable for a communication method used in the first network 98, the second network 99 or the like communication network may, for example, be selected by the communication module 90 among the plurality of antennas. The signal or power may be transmitted or received between the communication module 90 and the external electronic apparatus through at least one selected antenna. According to an alternative embodiment, another part (e.g., a radio frequency integrated circuit (RFIC)) may be additionally formed as a part of the antenna module 94 in addition to the radiator.

According to various embodiments, the antenna module 94 may form an mmWave antenna module. According to yet another embodiment, the mmWave antenna module may include a PCB, an RFIC disposed on or adjacent to a first side (e.g., a bottom side) of the PCB and supporting a designated high-frequency band (e.g., a mmWave band), and a plurality of antennas (e.g., an array antenna) disposed on or adjacent to a second side (e.g., a top or lateral side) of the PCB and transmitting the designated high-frequency band.

At least some among the elements may be connected to each other through a communication method between peripheral devices (e.g., a bus, a general-purpose input and output (GPIO), a serial peripheral interface (SPI), or a mobile industry processor interface (MIPI)).

According to yet another embodiment, a command or data may be transmitted or received between the electronic apparatus 100 and the external electronic apparatus 103 through the server 104 connected to the second network 99. Each external electronic apparatus 102 or 103 may be the same or different type of apparatus as or from the electronic apparatus 100. According to yet another embodiment, all or some of the operations executed in the electronic apparatus 100 may be performed in one or more external electronic apparatuses among the external electronic apparatuses 102, 103 or 104. For example, when the electronic apparatus 100 has to perform a certain function or service automatically or in response to a request from a user or another apparatus, the electronic apparatus 100 may request one or more external electronic apparatuses to perform at least a part of the function or service instead of or in addition to autonomously performing the function or service. One or more external electronic apparatuses that have received the request may execute at least a part of the requested function or service or an additional function or service related to the request, and transmit a result of the execution to the electronic apparatus 100. The electronic apparatus 100 directly or additionally processes the result, and provide the processed result as at least a part of the response. To this end, for example, cloud computing, distributed computing, mobile edge computing (MEC), or client-server computing technologies may be used. The electronic apparatus 100 may, for example, provide the ultralow-latency service based on the distributed computing or the MEC. According to an alternative embodiment, the external electronic apparatus 103 may include an IoT device. The server 104 may be an intelligent server based on machine learning and/or neural network. According to yet another embodiment, the external electronic apparatus 103 or the server 104 may be included in the second network 99. The electronic apparatus 100 may be applied to an intelligent service (e.g., smart home, a smart city, a smart car, or healthcare) based on the 5G communication technology and the IoT related technologies.

Figure 3:
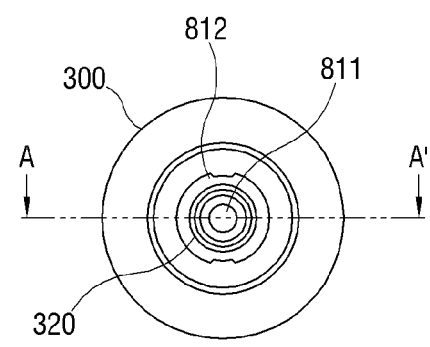
FIG. 3 shows a plan view and a cross-sectional view of a sensor and a cover in an electronic apparatus according to an embodiment of the disclosure.
Figure 3:
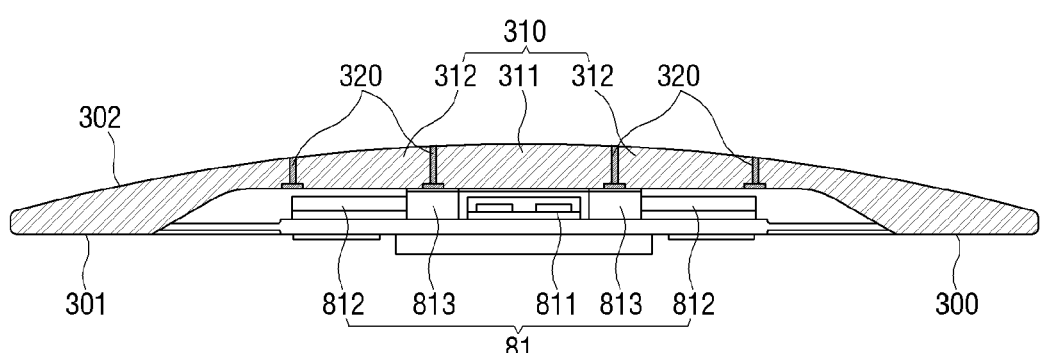

FIG. 3 shows a plan view and a cross-sectional view of a sensor and a cover in an electronic apparatus according to an embodiment of the disclosure. The cross-sectional view shown at the lower side of FIG. 3 is taken in the direction of A-A' of the plan view shown at the upper side.

Referring to FIG. 3, the cover 300 may be disposed at a side opposite to the display module 50 of the electronic apparatus 100. In other words, when a direction in which the display module 50 displays information is directed toward the front of the electronic apparatus 100, the cover 300 may be provided on the rear of the electronic apparatus 100.

The side of the cover 300 facing the sensor module 80 mounted to the inside of the electronic apparatus 100 will be referred to as an inner surface 301, and the opposite side of the cover 300 to be in contact with a user's wrist will be referred to as the outer surface 302. The outer surface 302 of the cover 300 may have a convex shape having curvature.

In more detail, the cover 300 and the sensor module 80 according to an embodiment of the disclosure will be described.

The cover 300 according to another embodiment of the disclosure may be made of a transparent material to transmit light output from the sensor module 80 or input to the sensor module 80. Therefore, the cover 300 may include a transparent layer 310 made of transparent plastic. The transparent plastic may, for example, include at least one of polyethylene terephthalate (PET), poly methyl methacrylate (PMMA) or a combination thereof.

Further, the outer surface of the cover 300 may have a curved surface to enhance a user's wearing comfort and increase light transmittance. When plastic is used as the material of the transparent layer 310, the transparent layer 310 may be processed to have various shapes while having the light transmittance and may not decrease in light transmittance even though it is notched. Due to the curvature of the outer surface 302 of the transparent layer 310, the transparent layer 310 is not easily broken by external impact even though it is decreased in thickness. The transparent layer 310 is less likely to be decreased in light transmittance by damage or scratches during the process, thereby having high manufacturing yields, and being suitable for mass production because the manufacturing costs of a plastic material are low.

Further, in relation to a partition wall 320 (to be described later), the transparent layer 310 made of plastic may facilitate the installation of the partition wall 320 into the transparent layer 310 when the transparent layer 310 is processed.

According to yet another embodiment of the disclosure, the sensor module 80 includes an optical sensor 81, and the optical sensor 81 may include a light emitting unit 811, and a light receiving unit 812. According to various embodiments, the optical sensor 81 may include a photoplethysmography (PPG) sensor capable of detecting a signal related to a user's cardiac impulses. Besides, the sensor module 80 may further include a sensor for detecting a signal related to various pieces of biometric information.

The light emitting unit 811 may include various devices capable of emitting light, for example, a light emitting diode (LED), an organic light emitting diode (OLED), or the liked device.

The light receiving unit 812 may include a light receiving device that can convert optical energy into electrical energy, for example, a photodiode.

According to yet another embodiment of the disclosure, the processor 10 may control the optical sensor 81 so that the light emitting unit 811 can emit light to reach a user's body and the light receiving unit 812 can receive the light reflected from the user's body. The processor 10 may acquire biometric information based on the signal related to biometric information received through the light receiving unit 812.

There may be a plurality of light receiving units 812 arranged around the light emitting unit 811, but not limited thereto. Alternatively, the light emitting unit 811 and the light receiving unit 812 may be arranged having various structures.

To make the optical sensor 81, such as the PPG, to operate properly, light emitted from the light emitting unit 811 does not enter the light receiving unit 812 while passing through the cover 300, but is required to enter the light receiving unit 812 after reaching and being reflected from a user's body. However, when the light emitting unit 811 and the light receiving unit 812 are not sufficiently physically separated, and a distance between lights is short compared to the wavelength of the light, interference (or crosstalk) may occur. The interference (or crosstalk) causes an optical loss, thereby lowering the optical efficiency of the optical sensor 81.

To address this problem, the cover 300 may include at least one partition wall 320 to separate a light transmission path, i.e., to partition the transparent layer 310. The transparent layer 310 is made of first plastic having light transmittance and disposed to cover the optical sensor 81. The first plastic may include at least one of PET, PMMA, or a combination thereof, as the main material of the cover 300 mentioned above. The transparent layer 310 may have light transmittance high enough to make the light emitted from the light emitting unit 811 pass through the transparent layer 310 and reach a user's body and make the light reflected from the user's body pass through the transparent layer 310 and reach the light receiving unit 812.

According to yet another embodiment of the disclosure, the partition wall 320 may be made of second plastic having lower light transmittance than the first plastic. In this case, the light transmittance lower than that of the first plastic may refer to the light transmittance low enough to prevent optical interference between the light emitting unit 811 and the light receiving unit 812. According to various embodiments of the disclosure, the partition wall 320 may be made of, for example, an opaque material to completely prevent the optical interference.

By the partition wall 320, the transparent layer 310 may be separated into a first transparent layer 311 through which light emitted from the light emitting unit 811 to detect a signal related to the biometric information passes, and a second transparent layer 312 through which light entering the light receiving unit 812 passes. Therefore, the light emitting unit 811 may be disposed at a position corresponding to the first transparent layer 311, and the light receiving unit 812 may be disposed at a position corresponding to the second transparent layer 312.

Referring to the plan view of FIG. 3, the optical sensor 81 may have a structure where the light receiving unit 812 circularly surrounds the light emitting unit 811, and the partition wall 320 is circularly formed in the transparent layer 310 between the light emitting unit 811 and the light receiving unit 812. In other words, the partition wall 320 formed circularly may be provided to surround the first transparent layer 311, and the second transparent layer 312 may be provided to surround the partition wall 320.

In this case, as shown in the cross-sectional view of FIG. 3, the optical sensor 81 itself may be structured to additionally include a partition wall 813 for separating the light emitting unit 811 and the light receiving unit 812 from each other.

Therefore, the partition wall 320 prevents the optical interference between the light emitted from the light emitting unit 811 and the light received in the light receiving unit 812. The number and shape of partition walls 320 may be varied depending on the light emitting unit 811 and the light receiving unit 812 of the optical sensor 81.

If the transparent layer 310 is made of glass, additional processing such as hole processing in the glass may be required to form the partition wall 320, and there may be difficulty in the processing and a risk of the damage as described above.

According to various embodiments of the disclosure, unlike other materials, plastic may facilitate the manufacture of the cover 300 based on a two-shot injection molding method. A method of manufacturing an electronic apparatus including the cover 300 will be described later in detail with reference to FIG. 12.

According to yet another embodiment of the disclosure, the lights passing through the transparent layer 310 are separated by the partition wall 320 and not lost, thereby more efficiently receiving the signal related to the biometric information acquired through the sensor module 80. In addition, the cover 300 according to various embodiments of the disclosure is easily processible and durable because the cover 300 is made of plastic.

Figure 4:
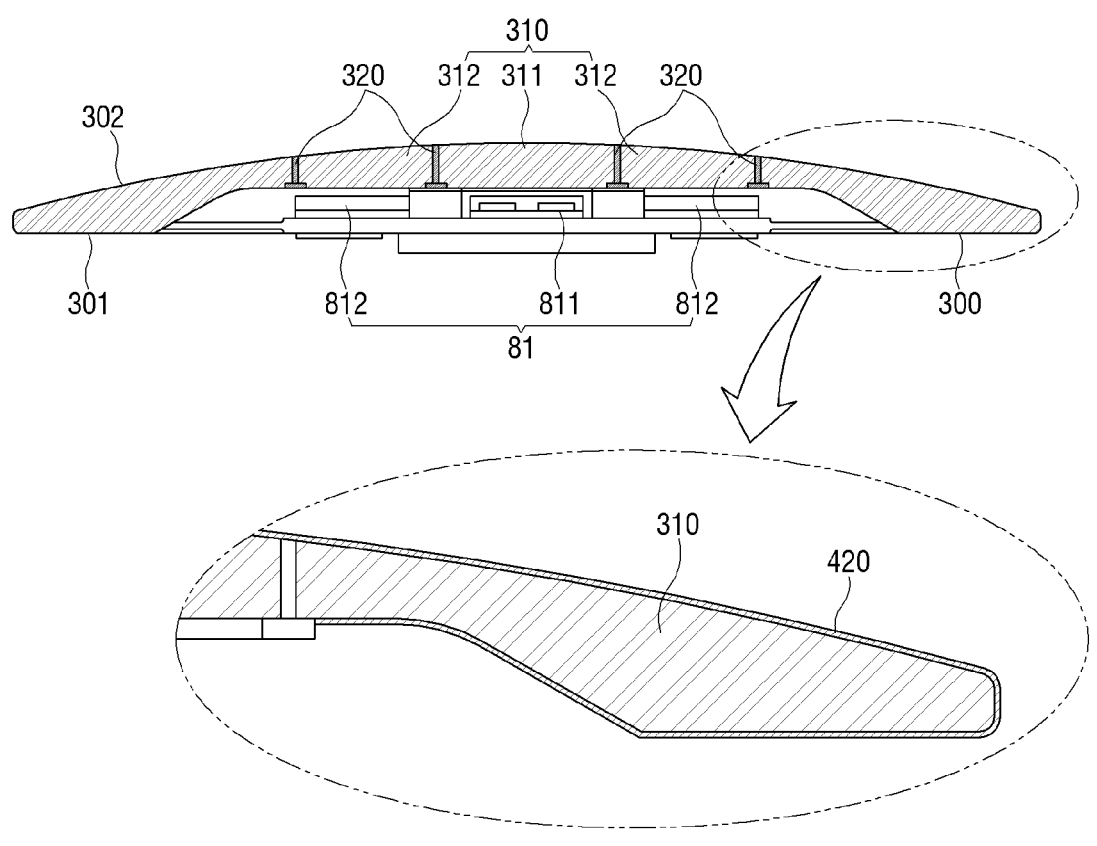
FIG. 4 is a cross-sectional view of a cover in an electronic apparatus according to an embodiment of the disclosure.

FIG. 4 is a cross-sectional view of a cover in an electronic apparatus according to an embodiment of the disclosure. The cross-sectional view shown in FIG. 4 is taken in the direction of A-A' of the plan view shown at the upper side of FIG. 3.

Referring to FIG. 4, the cover 300 may further include a first coating layer 420 provided on the outer surface of the transparent layer 310 and made of a material having a higher strength than the transparent layer 310.

The first coating layer 420 is to strengthen the surface hardness of the transparent layer 310 so that the transparent layer 310 may be improved in physical properties against external impact and prevented from thermal deformation, and may be made of a hard and processible material. In this case, the first coating layer 420 may be made of a transparent material having light transmittance like the transparent layer 310.

According to various embodiment, the main material of the first coating layer 420 may include polysilazane, sapphire, $SiO_2$, or the like coating material for enhancing the hardness. Besides, the first coating layer 420 may be made of various materials.

According to an embodiment of the disclosure, the cover 300 including the first coating layer 420 is further strengthened in surface hardness, thereby increasing the durability and decreasing the thermal deformation.

Figure 5:
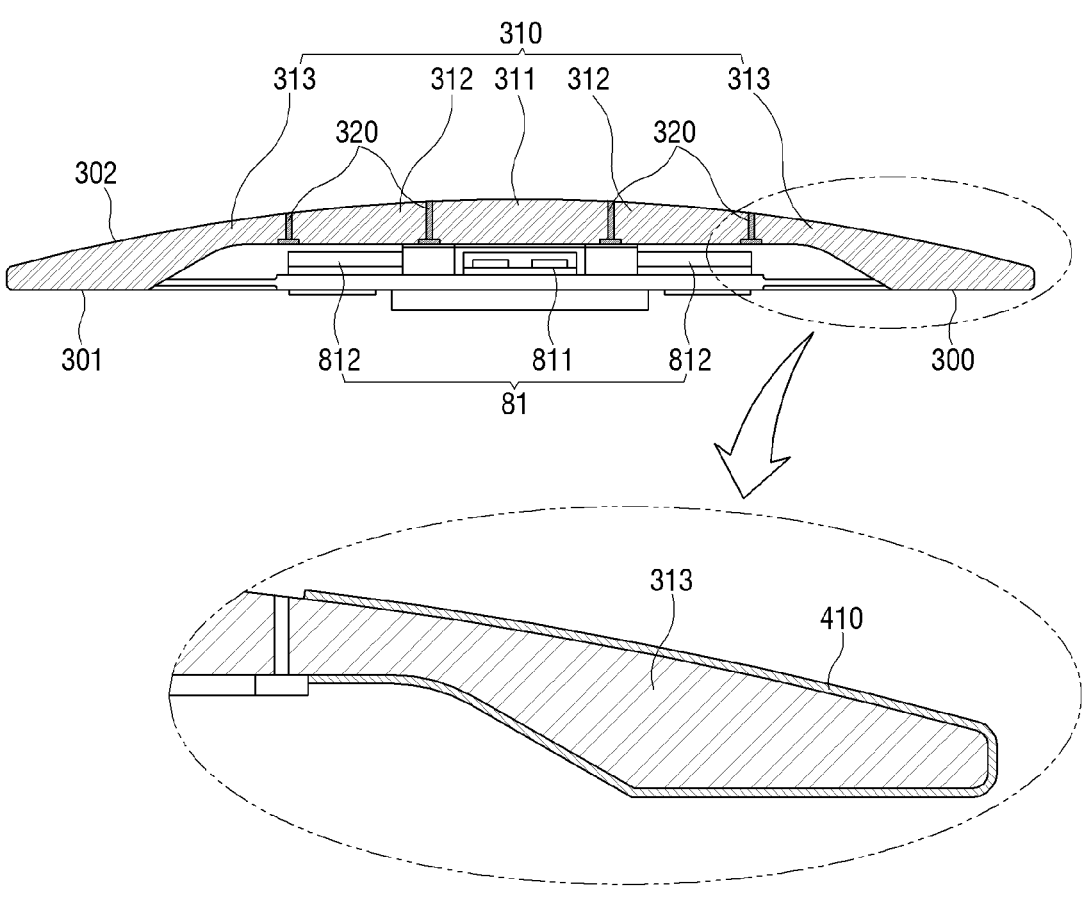
FIG. 5 is a cross-sectional view of a cover in an electronic apparatus according to an embodiment of the disclosure.

FIG. 5 is a cross-sectional view of a cover in an electronic apparatus according to an embodiment of the disclosure. The cross-sectional view shown in FIG. 5 is taken in the direction of A-A' of the plan view shown at the upper side of FIG. 3.

Referring to FIG. 5, the cover 300 may further include an electrode layer 410 provided on the outer surface of the transparent layer 310 to detect a signal related to the biometric information.

According to an embodiment of the disclosure, the sensor module 80 may further include an electrode sensor for detecting a signal related to biometric information in addition to the optical sensor 81. According to various embodiments, the electrode sensor may be an electrocardiogram (ECG) sensor capable of detecting a signal related to a user's cardiac impulses. The electrode layer 410 refers to a portion of the electrode sensor to be in contact with a user's body for the operations of the electrode sensor, and the electrode sensor may include wiring for power supply, and/or a circuit board for control in addition to the electrode layer 410. The processor 10 may further acquire biometric information based on a signal related to the biometric information received through the electrode layer 410.

A structure where the electrode layer 410 is provided on the transparent layer 310 of the cover 300 is as follows.

The signal related to the biometric information received from the electrode layer 410 is different from the signal related to the biometric information received from the optical sensor 81. The optical sensor 81 needs to transmit an optical signal to perform operations. When the electrode layer 410 is made of metal, metal may be an opaque material. Therefore, a signal transceiving area of the optical sensor 81 may be disposed not to overlap a signal transceiving area of the electrode layer 410.

For example, as shown in FIG. 5, the transparent layer 310 may further include a third transparent layer 313 disposed outside the second transparent layer 312, in addition to the first transparent layer 311 and the second transparent layer 312 through which the light emitted from the optical sensor 81 and the light emitted to the optical sensor 81 pass. The electrode layer 410 may be disposed on the outer surface of the third transparent layer 313 so as not to overlap with the signal transceiving area of the optical sensor 81. The electrode layer 410 is not limited to that shown in FIG. 5, but may be modified variously.

When the electrode layer 410 is disposed at the outermost side of the cover 300, the electrode layer 410 may be made of a material excellent in mechanical and chemical properties in addition to electrical properties because it will be in contact with the wrist. This is because the electrode layer 410 may be damaged by friction with the outside. For example, the electrode layer 410 may be made of a material that has strong corrosion resistance to prevent corrosion due to sweat from the wrist and does not irritate skin while it is in contact with the skin. According to another embodiment of the disclosure, the electrode layer 410 may be made of a material such as Cr, Ti, and/or CrSiCN.

However, various embodiments of the disclosure are not limited to the foregoing description, and the electrode layer 410 may be made of a material having both light transmittance and conductivity. For example, the electrode layer 410 is made of indium tin oxide (ITO), graphene, silver nanowire, and/or carbon nanotube (CNT). In this way, when the electrode having the light transmittance is used, the electrode layer 410 may be disposed on the transparent layer 310 without limitation.

According to yet another embodiment of the disclosure, the cover 300 may be the electrode layer 410 as well as the optical sensor 81 to acquire the biometric information, thereby acquiring the biometric information through more diverse routes.

Figure 6:
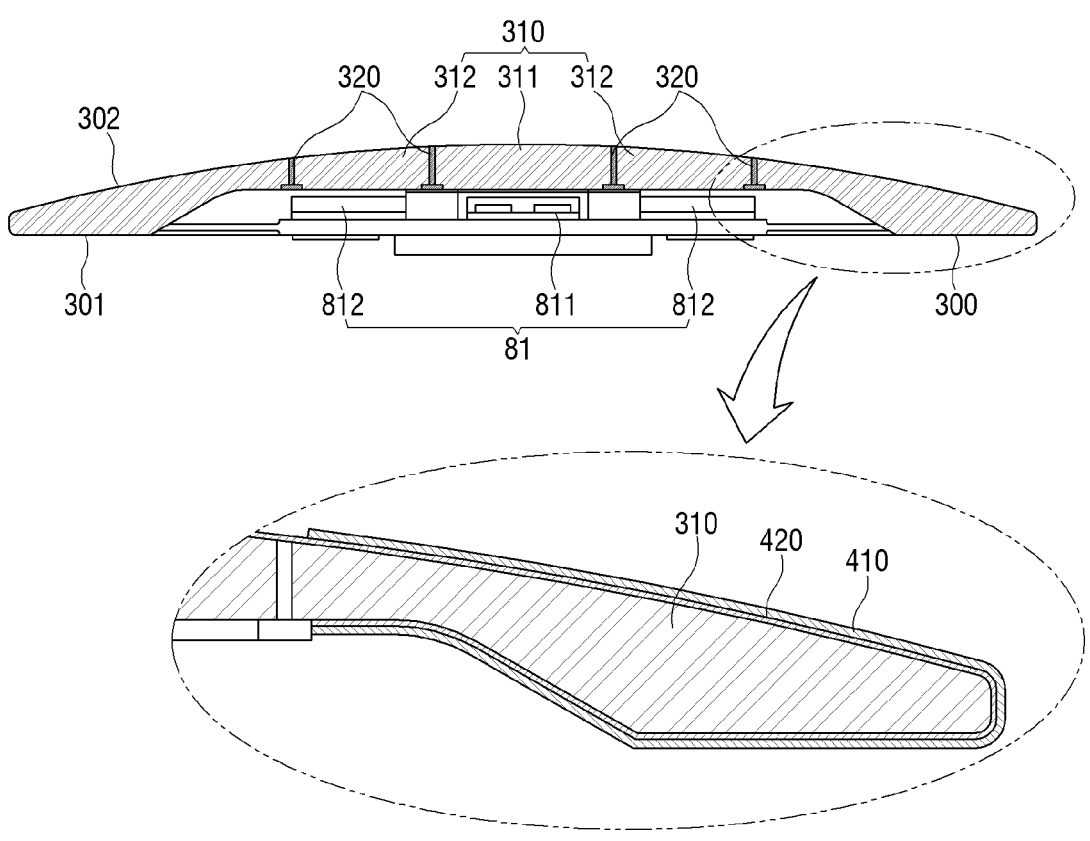
FIG. 6 is a cross-sectional view of a cover in an electronic apparatus according to an embodiment of the disclosure.

FIG. 6 is a cross-sectional view of a cover in an electronic apparatus according to an embodiment of the disclosure.

Referring to FIG. 6, the cover 300 in which the first coating layer 420 and the electrode layer 410 described with reference to FIGS. 4 and 5 are stacked in sequence on the transparent layer 310. According to an embodiment of the disclosure, the first coating layer 420 and the electrode layer 410 may have the same or similar configuration to the first coating layer 420 and the electrode layer 410 described with reference to FIGS. 4 and 5.

According to another embodiment of the disclosure, the cover 300 may further include the first coating layer 420 provided between the transparent layer 310 and the electrode layer 410 and made of a material having higher strength than the transparent layer 310.

The first coating layer 420 may include an adhesive material between the transparent layer 310 and the electrode layer 410, so that the first coating layer 420 can connect the transparent layer 310 and the electrode layer 410 more strongly. Further, the electrode layer 410 is stacked on the first coating layer 420, thereby increasing conductivity with low resistance and increasing the durability of the electrode layer 410.

Figure 7:
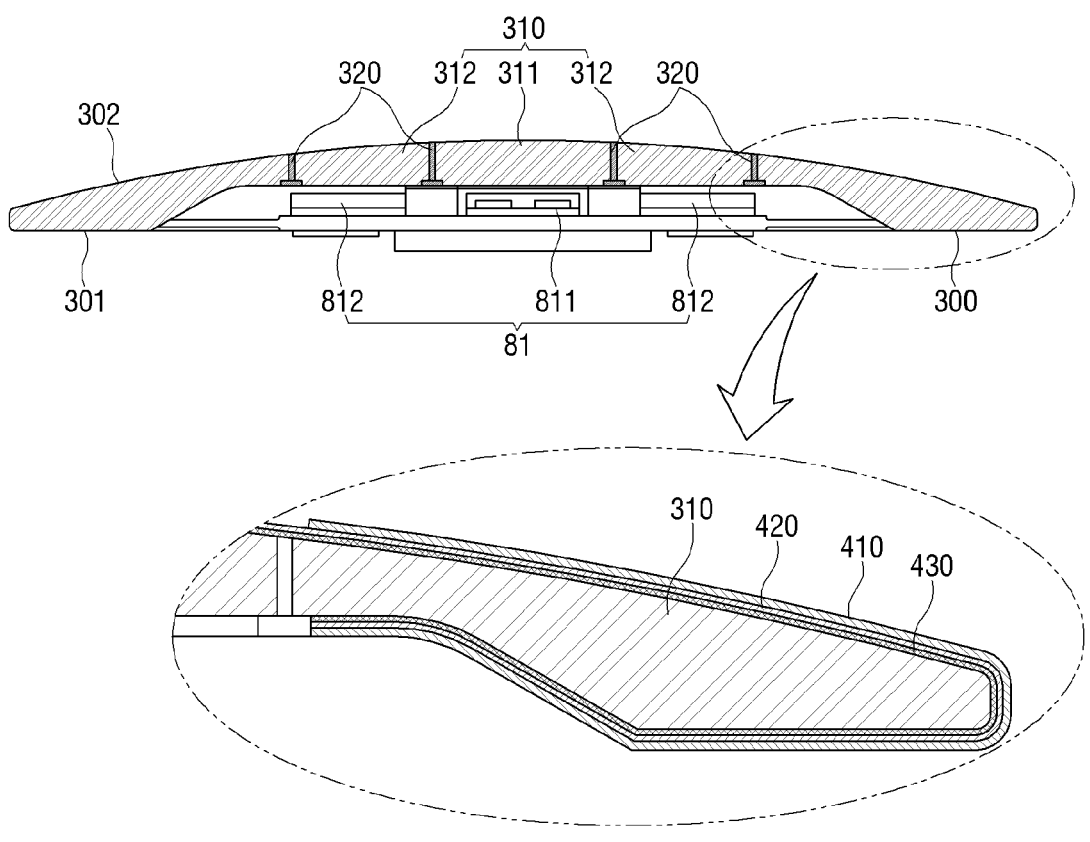
FIG. 7 is a cross-sectional view of a cover in an electronic apparatus according to an embodiment of the disclosure.

FIG. 7 is a cross-sectional view of a cover in an electronic apparatus according to an embodiment of the disclosure.

Referring to FIG. 7, the cover 300 further includes a second coating layer 430. FIG. 7 illustrates the cover 300, in which the second coating layer 430, and the first coating layer 420 and the electrode layer 410 described with reference to FIGS. 4 to 6 are stacked in sequence on the transparent layer 310. The second coating layer 430 may be provided between the transparent layer 310 and the first coating layer 420 and made of an adhesive material.

The second coating layer 430 may be formed of a wet coating material. For example, the second coating layer 430 may be formed of a silicon compound having adhesive properties on the outer surface of the transparent layer 310. By coating the outer surface of the transparent layer 310 with the second coating layer 430, it is possible to protect the outer surface from scratches or flaws due to contact with an object, and prevent the strength from being deteriorated due to the flaws.

In addition, the second coating layer 430 may serve to enhance adhesion between the transparent layer 310 and the first coating layer 420. According to an embodiment of the disclosure, the second coating layer 430 may assist the first coating layer 420 to primarily protect the transparent layer 310 and further prevent easy separation between the transparent layer 310 and the first coating layer 420.

According to another embodiment of the disclosure, the cover 300 includes the first coating layer 420 and the second coating layer 430 to improve the strength of the outer surface, protect the sensor module 80, and make the transparent layer 310 and the electrode layer 410 adhere to each other, thereby increasing the conductivity with low resistance and guaranteeing the durability.

Figure 8:
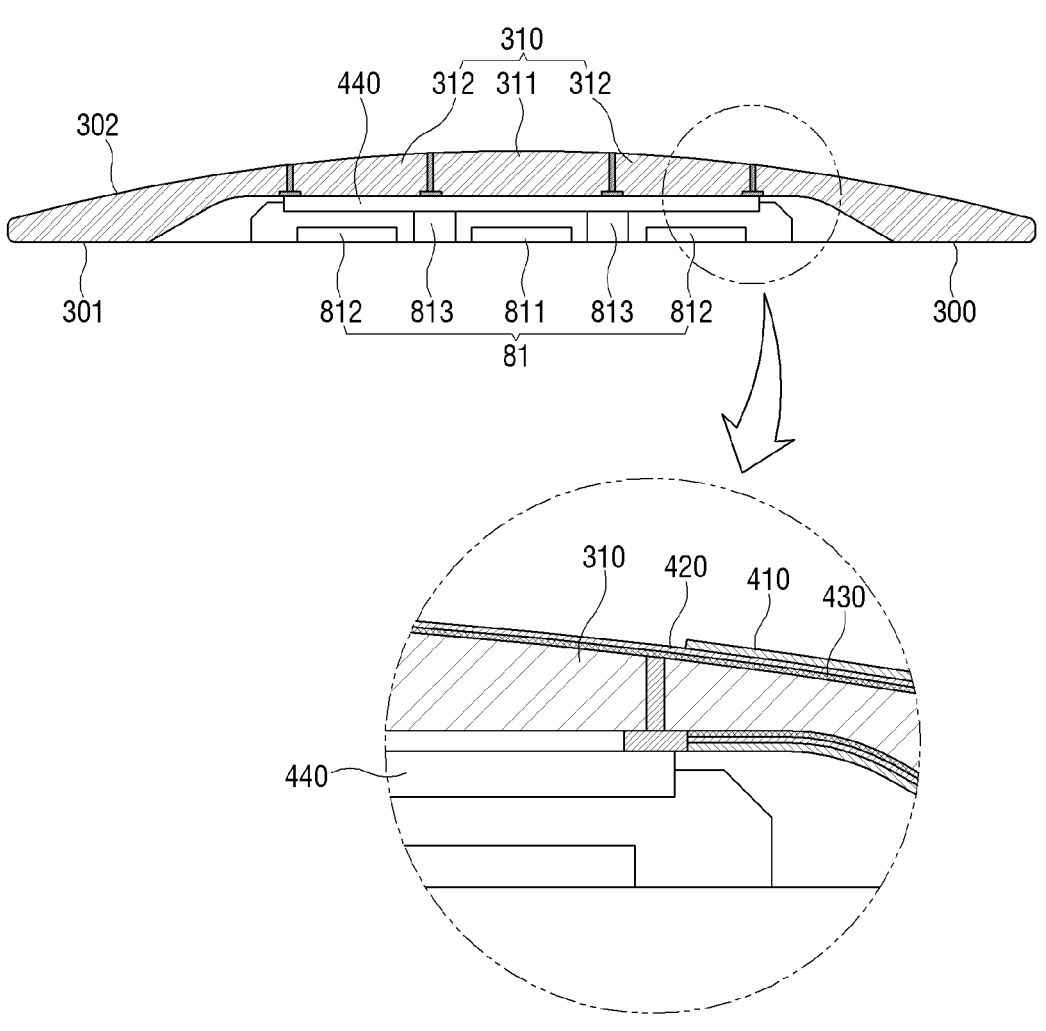
FIG. 8 is a cross-sectional view of a cover in an electronic apparatus according to an embodiment of the disclosure.

FIG. 8 is a cross-sectional view of a cover in an electronic apparatus according to an embodiment of the disclosure.

Referring to FIG. 8, the transparent layer 310 may include a third coating layer 440 formed on the inner surface 301 facing the optical sensor 81 and preventing the interference between the light passing through the first transparent layer 311 and the light passing through the second transparent layer 312. Therefore, the cover 300 may include the third coating layer 440 disposed on the inner surface 301 of the transparent layer 310 facing the optical sensor 81; and the first coating layer 420, the second coating layer 430, and the electrode layer 410 disposed as shown above in FIG. 7 on the outer surface 302 of the transparent layer 310. However, the coating layer or electrode layer disposed on the outer surface 302 of the transparent layer 310 is not limited to the foregoing description, but may be variously disposed as shown in FIGS. 4 to 6.

The third coating layer 440 may be translucent to enhance the aesthetics by making the disposed sensor module 80 invisible when viewed from the outer surface 302 of the cover 300, and maintain the light transmittance so that the optical sensor 81 can function properly. In other words, the third coating layer 440 may have a lower visible-light transmittance than and the same or similar light transmittance to the transparent layer 310.

The third coating layer 440 may be adjusted in haziness by changing the material and the thickness of the same material as the first coating layer 420 described above with reference to FIG. 4, and may be formed by bead processing, etching, or coating.

According to an embodiment of the disclosure, when polysilazane is used to adjust the translucency of the third coating layer 440, the translucency is adjustable through modification of chemical bonds without changing a physical shape, thereby maintaining the light transmittance.

According to various embodiment, perhydropolysilazane (PHPS) may be an inorganic polymer with a repeating unit of "—(SiH$_2$—NH)—" composed of only Si—H, N—H and Si—N without containing carbon.

When perhydropolysilazane coated on the transparent layer 310 is subjected to heat treatment at a certain temperature or higher in an ammonia atmosphere, Si—H bonds are replaced by Si—N bonds, thereby causing a difference in translucency due to a degree of Si—N bonds (surface roughness) and reaction time. This method is related to change in the material itself, and does not cause change in a physical shape unlike the mechanical methods such as bead processing, etching or coating, thereby maintaining the light transmittance and reducing an optical loss.

Therefore, the light emitted from the light emitting unit 811 of the sensor module 80 passes through the third coating layer 440 and is then irradiated to a user's body through the first transparent layer 311 of the transparent layer 310. In this case, the amount of light emitted from the light emitting unit 811 is hardly lost in the third coating layer 440.

For reference, in the case of an optical film with improved visibility to make the optical sensor maintain the transmittance and prevent an internal circuitry from being seen from the outside, the film itself is expensive, and therefore the electronic apparatus 100 may be increased in manufacturing costs and decreased in mass productivity.

On the other hand, the third coating layer 440 according to various embodiments of the disclosure is improved in visibility with inexpensive polysilazane, and has high transmittance to light related to the sensor module 80, thereby being superior to the optical film in terms of costs and quality.

According to various embodiments, the third coating layer 440 is made thinner than the existing film having the translucency, thereby eliminating the interference caused as light emitted from the light emitting unit 811 directly enters the light receiving unit 812.

Figure 9:
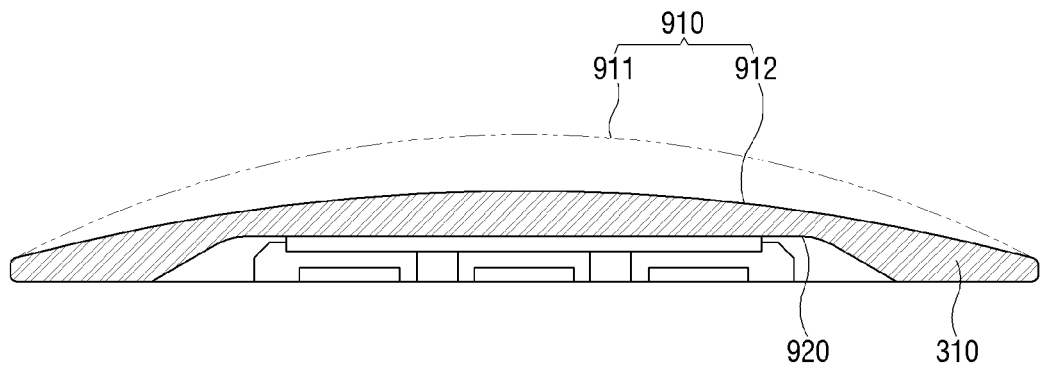
FIG. 9 is a cross-sectional view of a cover in an electronic apparatus according to an embodiment of the disclosure.

FIG. 9 is a cross-sectional view of a cover in an electronic apparatus according to an embodiment of the disclosure.

Referring to FIG. 9, the transparent layer 310 may have an outer surface 910, the curvature of which is based on at least one of a distance between the outer surface 910 of the transparent layer 310 and the optical sensor 81 and a contact area between the outer surface 910 of the transparent layer 310 and a user's body.

In order for the optical sensor 81 to detect a user's biometric information more accurately, a distance between the outer surface 910 of the transparent layer 310 and the optical sensor 81 needs to be kept as short as possible. By making the outer surface 910 of the transparent layer 310 closer to the optical sensor 81, the optical sensor 81 can more accurately process a signal related to cardiac impulses caused by motion artifact.

According to an embodiment of the disclosure, a recessed portion 920 may be formed in an inner surface 301 of the transparent layer 310 facing the optical sensor 81 in order to make the outer surface 910 of the transparent layer 310 closer to the optical sensor 81 and allow the sensor module 80 to be mounted therein.

Further, the outer surface 910 of the transparent layer 310 may be formed as a curved surface. Therefore, the larger the curvature of the outer surface 910 of the transparent layer 310, the thinner the transparent layer 310 from the center of the outer surface 910 to the periphery.

Meanwhile, in the case where the transparent layer 310 is made of glass, it may be difficult to make the transparent layer 310 have a large curvature and the transparent layer 310 may be easily broken due to the decreased thickness. On the other hand, in the case where the transparent layer 310 is made of plastic, it may be easy to make the transparent layer 310 have a large curvature and the transparent layer 310 is not easily broken even though it is varied in thickness.

Further, the smaller the contact area between the outer surface 910 the transparent layer 310 and a user's body, the more comfortable a user's wearing. Therefore, the larger the curvature of the outer surface 910 of the transparent layer 310, the more comfortable a user's wearing. This may also be applied even when at least one coating layer or electrode layer is stacked as described above with reference to FIGS. 4 to 7.

Referring again to FIG. 9, the transparent layer 310 including a first outer surface 911 and a second outer surface 912 which are different in curvature from each other. The first outer surface 911 of the transparent layer 310 has a larger curvature than the second outer surface 912, and thus the contact area between a user's body and the first outer surface 911 of the transparent layer 310 is smaller than that of the second outer surface 912. Therefore, the first outer surface 911 is improved in a user's wearing comfort. In this case, a distance between the outer surface 910 of the transparent layer 310 and the optical sensor 81 located at the center of the outer surface 910 becomes shorter in the second outer surface 912, thereby measuring a biometric signal more accurately in the second outer surface 912.

Therefore, the curvature of the outer surface 910 of the transparent layer 310 may be set based on the distance between the outer surface 910 of the transparent layer 310 and the optical sensor 81 and the contact area between the outer surface 910 of the transparent layer 310 and a user's body. In this case, the recessed portion 920 formed in the transparent layer 310 to reduce the distance between the outer surface 910 of the transparent layer 310 and the optical sensor 81 may also be taken into account to set the curvature.

Figure 10:
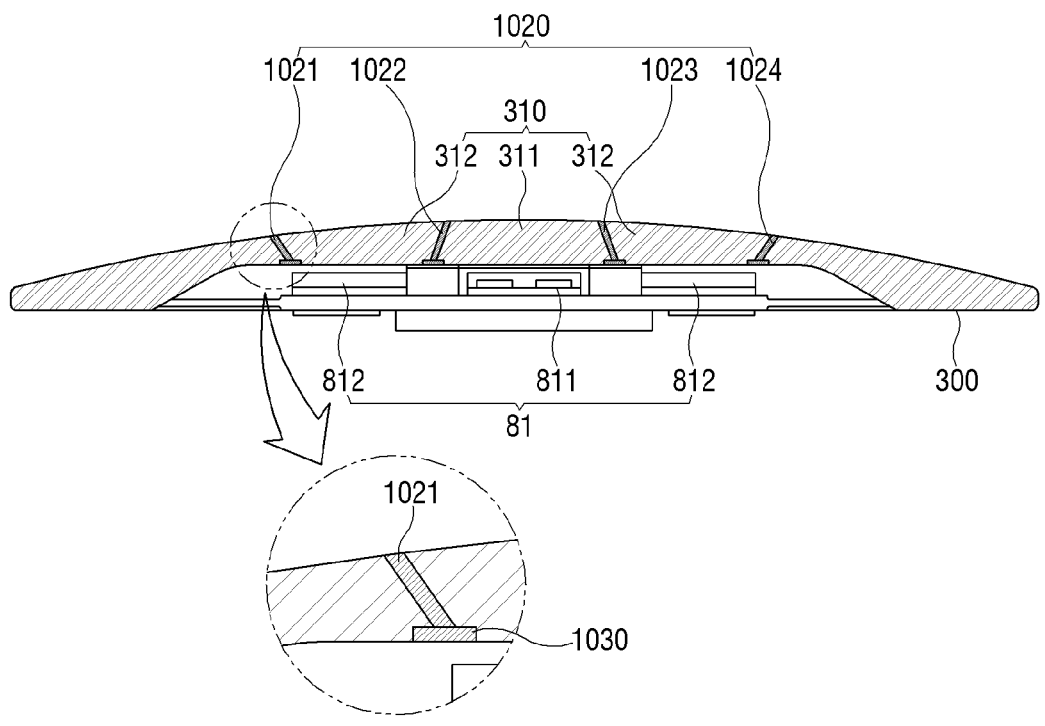
FIG. 10 is a cross-sectional view of a cover in an electronic apparatus according to an embodiment of the disclosure.

FIG. 10 is a cross-sectional view of a cover in an electronic apparatus according to an embodiment of the disclosure.

Referring to FIG. 10, a partition wall 1020, including partition walls 1021, 2022, 1023 and 1024, may each be formed at a predetermined angle (or view angle).

As the partition wall 1020 is formed at a certain angle, it is possible to reduce the amount of light generated from the light emitting unit 811 of the optical sensor 81 and entering the light receiving unit 812, or the amount of light coming from the outside. The partition wall 1020 may be disposed at a designated angle in the transparent layer 310 to maximize the efficiency of the optical sensor 81.

When the partition walls 1022 and 1023 are inclined toward the center of the light emitting unit 811, it is efficient to block the light coming from the outside, and it is possible to prevent light of the light emitting unit 811 from directly entering the light receiving unit 812.

In addition, the partition wall 1021 according to an embodiment of the disclosure may include an uneven portion 1030 shaped protruding perpendicularly to a direction in which the partition wall 1021 stands thereon. The uneven portion 1030 blocks the light as much as the area occupied by the uneven portion 1030 along the inner surface 301 of the transparent layer 310, thereby additionally preventing the light of the light emitting unit 811 from directly entering the light receiving unit 812, and forming a stable structure by supporting the inner surface 301 of the transparent layer 310 inside the transparent layer 310.

Figure 11:
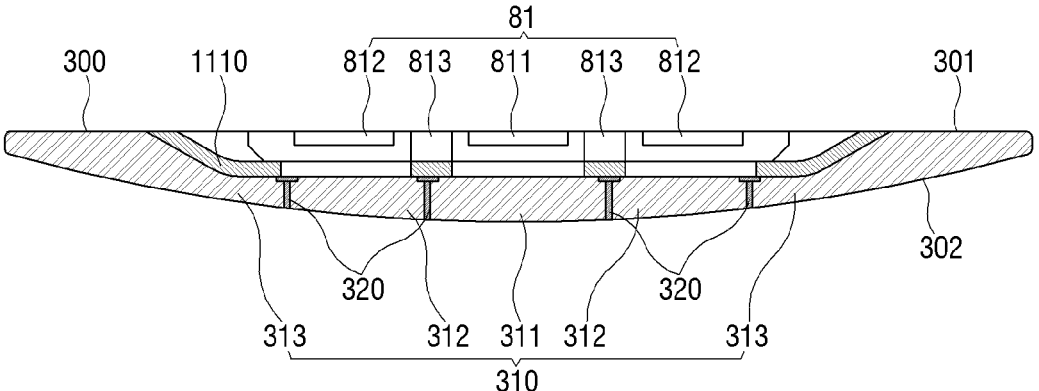
FIG. 11 is a cross-sectional view of a cover in an electronic apparatus according to an embodiment of the disclosure.

FIG. 11 is a cross-sectional view of a cover in an electronic apparatus according to an embodiment of the disclosure.

FIG. 11 shows that the outer surface 302 of the cover 300 faces downwards, unlike those of FIGS. 3 to 10.

Referring to FIG. 11, the transparent layer 310 may include a fourth coating layer 1110 provided on the inner surface 301 facing the optical sensor 81 and made of a material having lower light transmittance than the transparent layer 310. The fourth coating layer 1110 may also be applied even when at least one coating layer or electrode layer is stacked as described above with reference to FIGS. 4 to 7.

The fourth coating layer 1110 may be formed using black ink. The fourth coating layer 1110 restricts the passage of light emitted and going out of the light emitting unit 811 and light entering the light receiving unit 812, and blocks the light entering the light receiving unit 812 through the third transparent layer 313 disposed at the outer side of the second transparent layer 312, thereby increasing the optical efficiency of the optical sensor 81.

Further, the fourth coating layer 1110 is coated even between the partition wall 320 provided in the transparent layer 310 and the partition wall 813 provided in the optical sensor 81, thereby having an effect on additionally decreasing a phenomenon that the light emitted from the light emitting unit 811 directly enters the light receiving unit 812.

Figure 12:
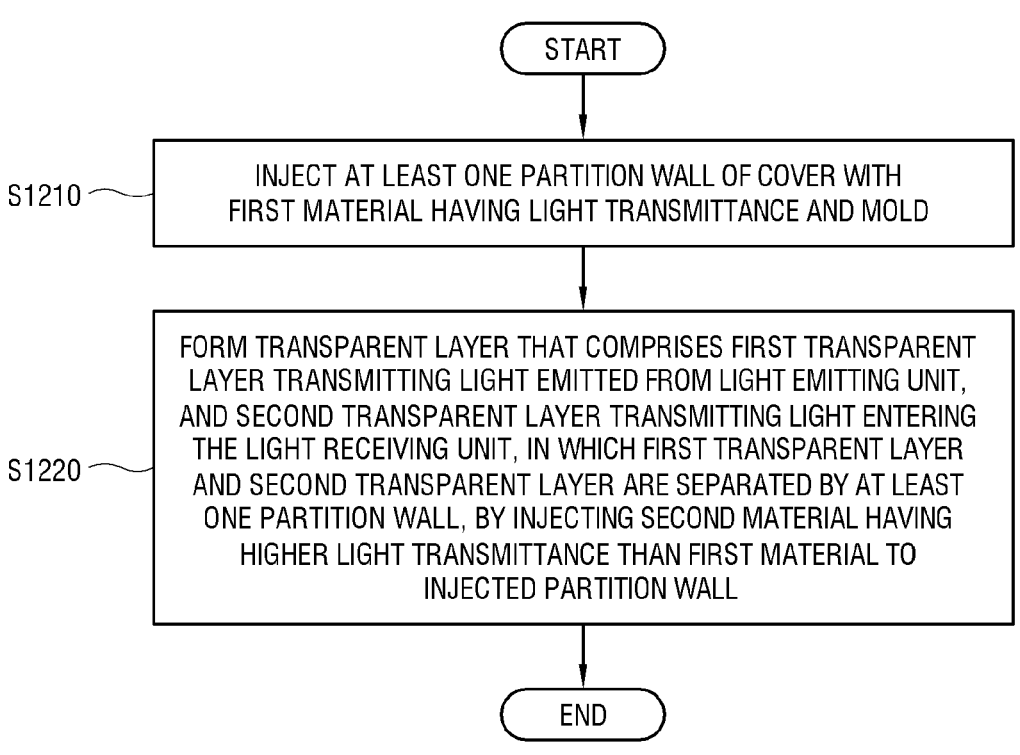
FIG. 12 is a flowchart of a method by which an electronic apparatus including a cover is manufactured according to an embodiment of the disclosure.

FIG. 12 is a flowchart of a method by which an electronic apparatus including a cover is manufactured according to an embodiment of the disclosure.

As described above with reference to FIG. 3, the cover 300 according to various embodiments of the disclosure may be manufactured with plastic based on a two-shot injection molding method.

The two-shot injection molding method refers to that different plastic materials are injected in sequence based on difference in hardening temperature, and is an ideal process for multiple materials and multi-color plastic products. With recent development of technology, various automatic injection technologies such as rotary, turntable, index core rotation, and spin-form methods have appeared, and are thus advantageous for mass production. Further, plastic is easily processed due to the nature of plastic.

Referring to FIG. 12, in a method of manufacturing the electronic apparatus 100 including the sensor 81 including the light emitting unit 811 and the light receiving unit 812 to detect a signal related to biometric information, and the cover 300 covering the sensor 81, at least one partition wall 320 for the cover 300 may be injected using a first material having light transmittance, and a mold at operation S1210. The first material may be the second plastic described with reference to FIG. 3.

A second material having higher light transmittance than the first material is injected into the injected partition wall 320, thereby forming the transparent layer 310 that includes the first transparent layer 311 through which light emitted from the light emitting unit 811 passes, and the second transparent layer 312 through which light entering the light receiving unit 812 passes, in which the first transparent layer 311 and the second transparent layer 312 are partitioned by at least one partition wall 320 at operation S1220. The second material may be the first plastic described with reference to FIG. 3. In this case, the first material and the second material may be plastics different in hardening temperature from each other.

According to an embodiment of the disclosure, the operation of forming the transparent layer 310 includes an operation of forming the transparent layer 310 that includes the third transparent layer 313 at the outer side of the second transparent layer 312, in which the second transparent layer 312 and the third transparent layer 313 are partitioned by at least one partition wall 320, and further includes an operation of coating the electrode layer 410 provided on the outer surface of the third transparent layer 313 to detect the second signal related to the biometric information.

Therefore, according to an embodiment of the disclosure, the cover 300 with the partition wall 320 readily provided inside the transparent layer 310 is manufactured by the two-shot injection molding method.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic apparatus comprising:
a sensor comprising a light emitter and a light receiver;
a transparent layer comprising:
    a first transparent layer comprising a first plastic having light transmittance, disposed to cover the sensor, the first transparent layer configured to transmit light emitted from the light emitter for detecting a signal related to biometric information, and
    a second transparent layer configured to transmit light entering the light receiver;
a cover comprising at least one partition wall comprising a second plastic having lower light transmittance than the first plastic and separating the first transparent layer and the second transparent layer from each other; and
a processor configured to acquire the biometric information based on the signal related to the biometric information received through the light receiver.

2. The electronic apparatus of claim 1, wherein the transparent layer comprises an outer surface having curvature based on at least one of a distance between the outer surface of the transparent layer and the sensor, or a contact area between the outer surface of the transparent layer and a user's body.

3. The electronic apparatus of claim 2, wherein the partition wall is disposed as inclined inside the transparent layer.

4. The electronic apparatus of claim 2, further comprising:
a first coating layer provided on the outer surface of the transparent layer and comprising a material having higher strength than the transparent layer.

5. The electronic apparatus of claim 1,
wherein the signal comprises a first signal,
wherein the electronic apparatus further comprises an electrode layer provided on an outer surface of the transparent layer,
wherein the electronic apparatus is configured to detect a second signal related to biometric information, and
wherein the processor is configured to receive the biometric information, through the electrode layer, the second signal related to the biometric information.

6. The electronic apparatus of claim 5, further comprising:
a first coating layer provided between the transparent layer and the electrode layer
wherein the first coating layer comprises a material having higher strength than the transparent layer.

7. The electronic apparatus of claim 6, wherein the first coating layer comprises an adhesive material between the transparent layer and the electrode layer.

8. The electronic apparatus of claim 6, further comprising:
a second coating layer provided between the transparent layer and the first coating layer
wherein the second coating layer comprises an adhesive material.

9. The electronic apparatus of claim 1, further comprising:
a third coating layer provided on an inner surface of the transparent layer facing the sensor, and
wherein the third coating layer comprises a material having lower visible-light transmittance than the transparent layer.

10. The electronic apparatus of claim 1, wherein the transparent layer comprises a recessed portion, which accommodates at least a portion of the sensor, on an inner surface facing the sensor.

11. The electronic apparatus of claim 1,
wherein the transparent layer comprises a fourth coating layer provided on an inner surface facing the sensor, and wherein the transparent layer comprises a material having lower light transmittance than the transparent layer.

12. The electronic apparatus of claim 1, wherein the partition wall comprises an uneven portion shaped protruding perpendicularly to a direction in which the partition wall stands at a first end thereof.

13. The electronic apparatus of claim 5,
wherein the transparent layer further comprises a third transparent layer at an outer side of the second transparent layer,
wherein the at least one partition wall is configured to separate the second transparent layer and the third transparent layer from each other, and
wherein the electrode layer is provided on an outer surface of the third transparent layer.

14. The electronic apparatus of claim 1, wherein the sensor comprises a partition wall disposed between the light emitter and the light receiver and separating the light emitter and the light receiver from each other.

15. The electronic apparatus of claim 13, wherein the electrode layer is formed from at least one of Cr, Ti or CrSiCN.

16. The electronic apparatus of claim 13, wherein the electrode layer is formed of at least one of indium tin oxide (ITO), graphene, silver nanowire, or carbon nanotube (CNT).

17. The electronic apparatus of claim 1,
wherein the transparent layer comprises a first outer surface and a second outer surface having a different in curvature from each other,
wherein the first outer surface has a larger curvature than the second outer surface.

18. A method of manufacturing an electronic apparatus that comprises a sensor comprising a light emitter and a light receiver to detect a signal related to biometric information, and a cover covering the sensor, the method comprising:
injecting at least one partition wall of the cover with a first material having light transmittance and a mold; and
forming a transparent layer that comprises:
a first transparent layer configured to transmit light emitted from the light emitter, and
a second transparent layer configured to transmit light entering the light receiver, in which the first transparent layer and the second transparent layer are separated by the at least one partition wall, by injecting a second material having higher light transmittance than the first material to the injected partition wall.

* * * * *